United States Patent
Tice

(10) Patent No.: US 7,232,512 B2
(45) Date of Patent: Jun. 19, 2007

(54) SYSTEM AND METHOD OF SENSITIVITY ADJUSTMENT FOR AN ELECTROCHEMICAL SENSOR

(75) Inventor: Lee D. Tice, Bartlett, IL (US)

(73) Assignee: Honeywell International, Inc., Morristown, NJ (US)

( * ) Notice: Subject to any disclaimer, the term of this patent is extended or adjusted under 35 U.S.C. 154(b) by 168 days.

(21) Appl. No.: 11/006,393

(22) Filed: Dec. 7, 2004

(65) Prior Publication Data

US 2006/0042350 A1   Mar. 2, 2006

Related U.S. Application Data

(63) Continuation-in-part of application No. 10/925,750, filed on Aug. 25, 2004.

(51) Int. Cl.
G01N 27/416 (2006.01)

(52) U.S. Cl. .............. 204/406; 204/400; 204/401; 73/23.21

(58) Field of Classification Search .............. 204/400, 204/401, 406, 431; 73/23.21; 123/693, 123/694, 695
See application file for complete search history.

(56) References Cited

U.S. PATENT DOCUMENTS

| | | | | |
|---|---|---|---|---|
| 4,472,262 A | * | 9/1984 | Kondo et al. | 204/408 |
| 4,701,253 A | * | 10/1987 | Ligtenberg et al. | 204/416 |
| 4,940,528 A | * | 7/1990 | Oki et al. | 204/427 |
| 6,049,283 A | * | 4/2000 | Lindsay | 340/635 |
| 6,279,372 B1 | * | 8/2001 | Zhang | 73/1.07 |
| 6,428,684 B1 | * | 8/2002 | Warburton | 205/775 |

FOREIGN PATENT DOCUMENTS

JP   2001-165890   *   6/2001
WO   WO 00/14523 A2   *   3/2000

* cited by examiner

Primary Examiner—Kaj K. Olsen
(74) Attorney, Agent, or Firm—Welsh & Katz, Ltd.

(57) ABSTRACT

A gas detector with a compensated electrochemical sensor exhibits altered sensitivity in response to decreasing sensitivity relative to both gas exposure and non-gas exposure. A sensitivity adjustment can be established in response thereto.

13 Claims, 2 Drawing Sheets

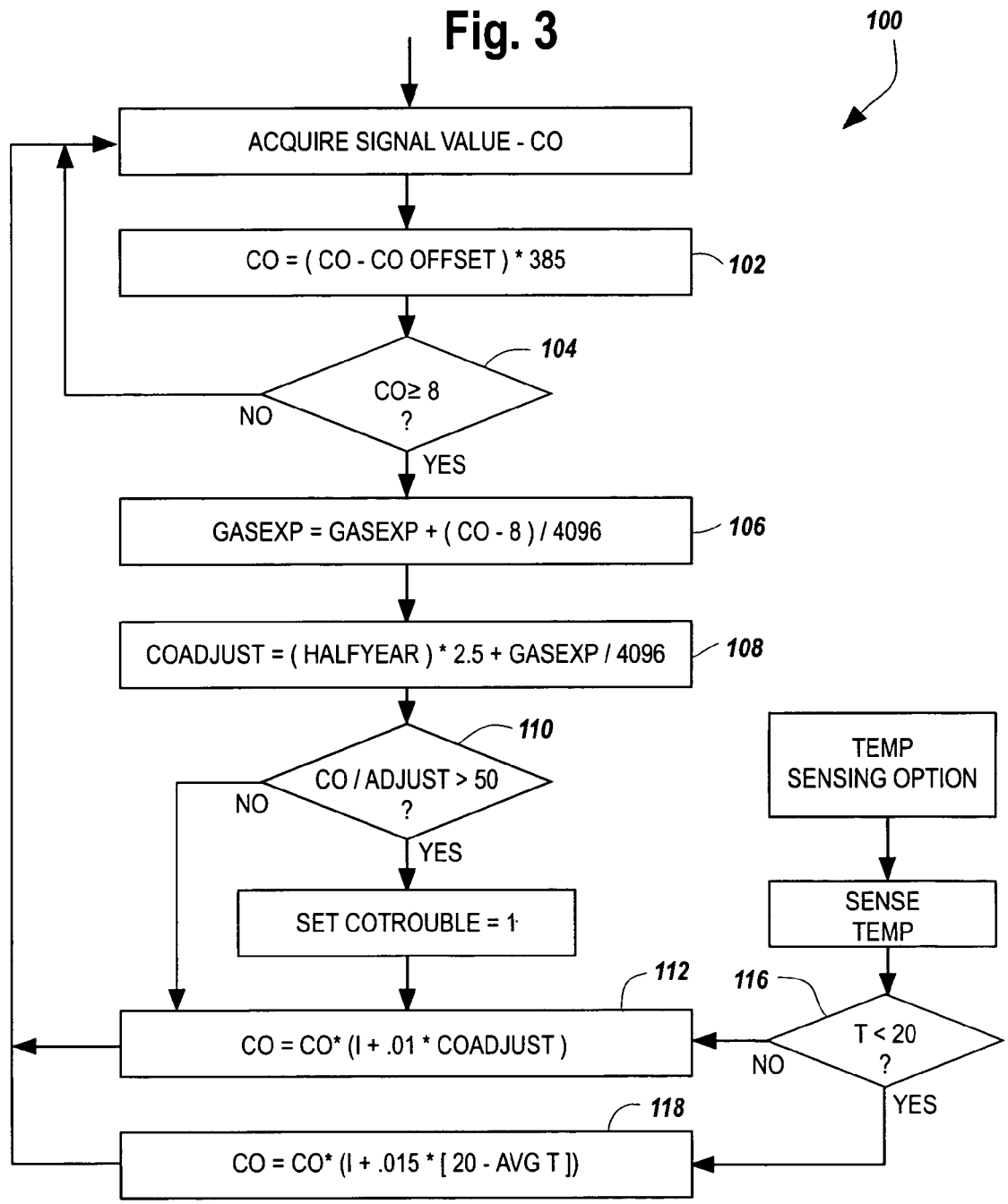

SYSTEM AND METHOD OF SENSITIVITY ADJUSTMENT FOR AN ELECTROCHEMICAL SENSOR

CROSS REFERENCE TO RELATED APPLICATION

This application is a continuation-in-part of U.S. patent application Ser. No. 10/925,750 filed Aug. 25, 2004 entitled "Self-Adjusting Electrochemical Sensor"

FIELD OF THE INVENTION

The invention pertains to gas detectors. More particularly, the invention pertains to gas detectors having sensitivity adjusted electro-chemical sensors.

BACKGROUND OF THE INVENTION

Depending on the circumstances it can be desirable and/or particularly important to be able to sense the presence of various gases which might be dangerous or explosive. These include carbon monoxide, carbon dioxide, propane, methane, as well as other potentially explosive gases.

A variety of sensors are known which can detect various gases. These sensors are based on different technologies and have different performance characteristics and different cost characteristics. One technology of ongoing interest is represented by electrochemical sensors. This class of sensors is potentially reliable and inexpensive.

Electrochemical sensors can be designed so as to be responsive to a gas of interest and to be highly sensitive. They respond to a gas of interest with a respective output current.

Advantages of electro-chemical sensors are that they are very robust and difficult to poison. Acid used in such sensors is such that the sensors can operate over a wide pH range. Another aspect of robustness of electro-chemical sensors relates to the amount of platinum used on the electrodes. The platinum can "wear" over time. This results in a change in sensitivity as a result of changing the surface and activity points in the sensor.

It is recognized that exposures to gases that cause a response in the sensor cause a slight decline in sensor sensitivity.

FIG. 1 illustrates sensitivity variations of a typical electrochemical sensor over time, for example, a period of years, with and without gas exposure. As is apparent from FIG. 1, where an electro-chemical sensor has been exposed to relatively high concentrations of gases, the sensitivity experiences a greater decline than is the case where the respective sensor has not been exposed to high concentrations of gas.

To realize the various benefits of using electro-chemical sensors, it would be desirable to be able to adjust the sensitivity over the lifetime operation of the respective sensor so as to maintain more consistent long-term performance of the respective sensors than would otherwise be possible. Preferably, such sensitivity monitoring and adjustments could be implemented in a variety of circuit configurations which incorporate electro-chemical sensors.

BRIEF DESCRIPTION OF THE DRAWINGS

FIG. 3 is a flow diagraph of signal processing in accordance with the invention.

DETAILED DESCRIPTION OF THE EMBODIMENTS

Figure 1:
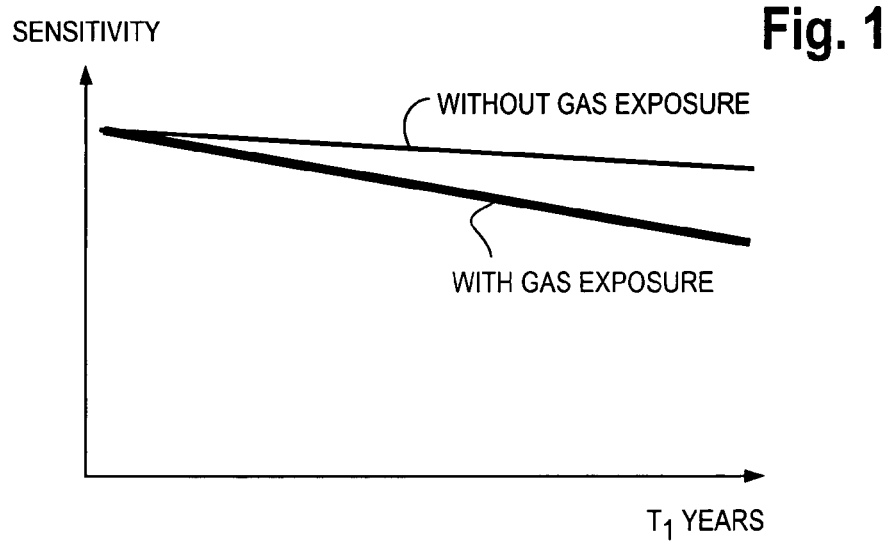
FIG. 1 is a graph of sensitivity variation as a function of time with and without gas exposure.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

A disclosed embodiment of the invention overcomes the problems with monitoring and adjusting the sensitivity of an electrochemical sensor as it ages over time. In addition, such processing functionality can be combined with signal processing of a type disclosed in the parent hereto, application Ser. No. 10/925,750 filed Aug. 25, 2004 and incorporated herein by reference.

In accordance with the invention, the past exposure of an electro-chemical sensor to various gases is monitored as reflected in signals generated by the sensor. A prediction of platinum "wear", or deterioration can be produced by the subject processing. In one aspect of the invention, the processing can be determined from accelerated testing using exposures to high concentrations of gases. Such concentrations cause activity at the platinum electrodes which produce the expected "wear" or deterioration over time which in turn produces the reduced sensitivity.

Lifetime information can be stored locally relative to the sensor. The associated signal processing can carry out a time-amplitude exposure integration function. Such processing can integrate the exposures that cause the performance deterioration of the electrodes over time. It can also incorporate various relationships predetermined from testing for the perdition of the platinum by the signals generated from the gas reactions. Temperature considerations can be incorporated into the processing as can humidity.

In yet another aspect of the invention, the processing can be combined with other available sensitivity adjusting methods to improve supervision capabilities. A predictable or gradual wearing over time of the platinum due to only low activity levels which result from little or no reactive gas being present can be taken into account.

In yet another aspect of the invention, filters may be used to block material that interferes with reaction of the platinum from entering the sensing chamber. The state of the filter or filters can be monitored to keep track of the material accumulated in the filter as it is blocked from entering the sensing chamber. In such instances, the filters can be replaced on an as needed basis. Alternately, the filters can be replaced periodically.

Further in accordance with the invention, processing which sums the exposures with and without gas to form total exposure accumulated over time, can be used to produce an adjustment which can compensate for both types of degrading of the sensor. Such compensation can also be used with other types of sensors, such as catalytic-type sensors which sense carbon monoxide, hydrocarbons or other gases in the atmosphere. Such compensation is advantageous in that any gas or element in the environment that causes a response from the respective electrochemical sensor can also be reflected in the adjustment processing. For example, where the electrochemical sensor is configured as a carbon monoxide sensor, the presence of gases such as iso-butane or propane can also be reflected in the adjustment processing.

One of the advantages of the present invention is that the noted processing can be incorporated into a variety of detectors having different circuit configurations which utilize electrochemical sensors. An exemplary detector into which the processing of the present invention can be incorporated is discussed subsequently. It will be understood that the particular detector is exemplary only and is not a limitation of the present invention.

Figure 2:
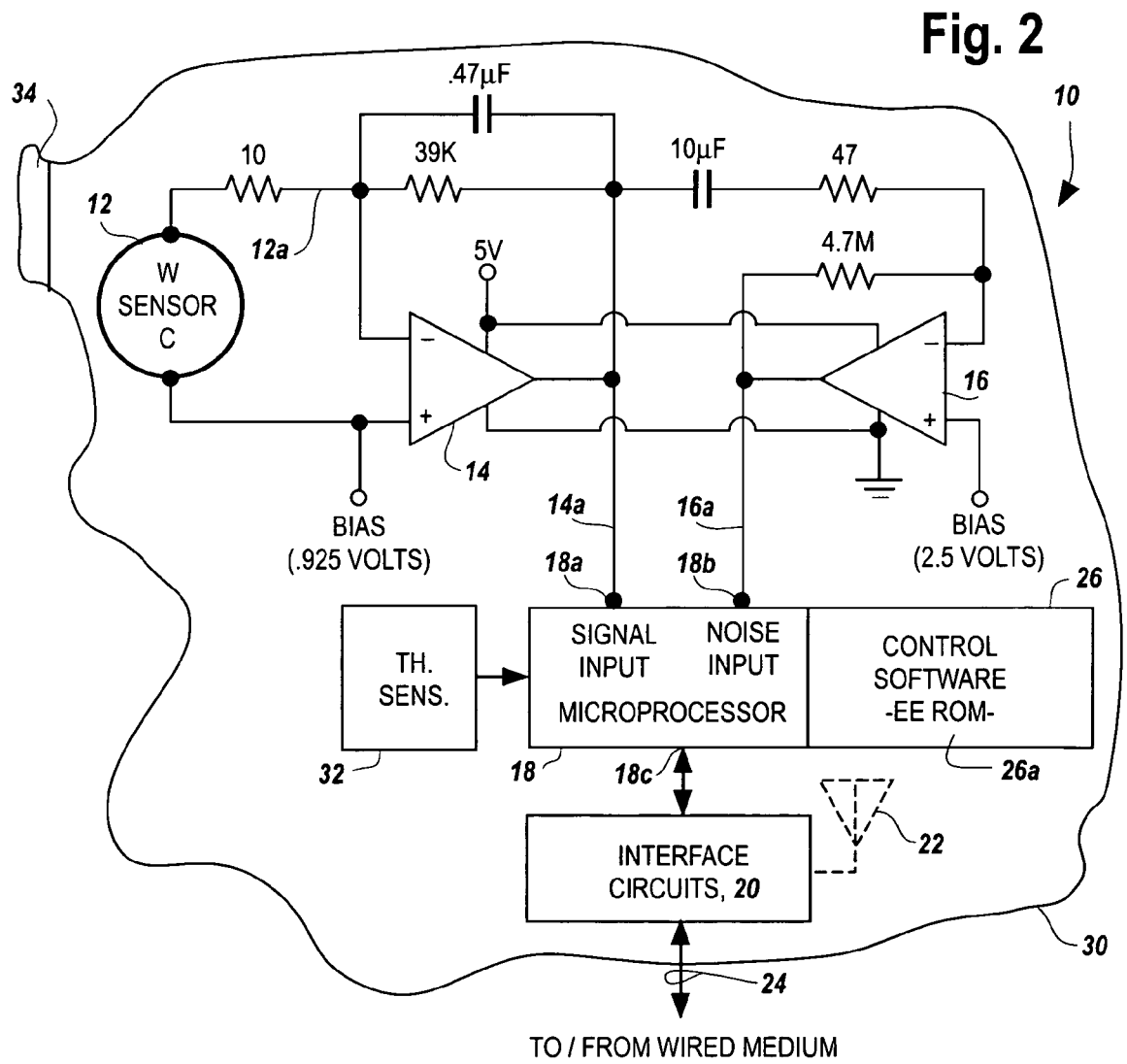
FIG. 2 is a block diagram of an exemplary detector in accordance with the invention.

Relative to FIG. 2, an exemplary gas detector 10 which embodies the processing of the present invention includes an electrochemical sensor 12 which has an output, line 12a, that is coupled to a pair of operational amplifiers 14, 16. The amplifier 14 provides a buffered output of the signal from sensor 12 and is configured as a relatively low pass filter and current-to-voltage converter, see FIG. 1, which is associated with the output signal from the sensor 12. An output 14a from operational amplifier 14 can be coupled to a sensor signal input port 18a of a programmable processor 18.

Operational amplifier 16 is configured as a high pass filter with additional gain and responds only to the high frequency noise in the signal from the operational amplifier 14, line 14a. The combination of the low pass characteristics of amplifier 14 and the high pass characteristics of amplifier 16 create a band pass for the noise. That signal is coupled, via line 16a, to a noise input port 18b of the processor 18. Processor 18 thus has access to a concentration signal, line 14a, and an associated noise signal, line 16a.

Processor 18 can in turn be coupled via output port 18c to interface circuits 20 as would be understood by those of skill in the art. Circuitry 20 can include an rf antenna, indicated in phantom, 22 for wireless configurations. Alternately, interface circuits 20 can couple signals to and from a wired medium 24. Detector 10 can thus communicate with an external alarm system, for example, as disclosed in Tice et al. U.S. Pat. No. 6,320,501 entitled "Multiple Sensor System for Alarm Determination with Device-to-Device Communications", assigned to the assignee hereof and incorporated herein by reference. It will be understood that neither of the detailed configurations of the interface circuits 20 nor the type of medium, wired or wireless, are limitations of the present invention.

Processor 18 operates in accordance with prestored control software 26 which could be stored, for example, in electrically eraseable read only memory EEPROM 26a. The detector 10 can be contained within and carried by a housing 30 as would be understood by those of skill in the art.

The detector 10 can also include a temperature or thermal sensor 32 whose output is coupled to processor 18. Using thermal sensor 32, temperature compensation can be incorporated into gas signal processing. As noted above, filter 34 can be included in detector 10 to exclude undesirable airborne matter in fluids.

The processor 18 in combination with control software 26 can carry out signal processing in response to signal inputs from sensor 12. Exemplary processing is discussed subsequently relative to FIG. 3.

FIG. 3 illustrates steps of a method 100 in accordance with the invention which could be used with the detector 10 as well as detectors of other circuit configurations. In accordance with method 100 of FIG. 3, in a step 102, output signals from the respective electrochemical sensor are converted to parts per million after removing both bias and offset. In a step 104, normal drift of the sensor 12 is taken into account and ignored if less than a predetermined threshold.

If the signal value is greater than or equal to a predetermined threshold such as the numeral 8 ppm, then in step 106 gas exposure is determined. Gas exposure GASEXP corresponds to cumulative exposures of gas samples over time which degrade the platinum and sensitivity of the respective sensor.

In a step 108 an adjustment value COADJUST is produced. Since CO sensors are not replaced in the field, no reset is needed. The portion of the processing equation of step 108 namely:

Half Year*2.5

Represents a 5% degrading of non-gas exposure related sensitivity per year. The portion of the processing in step 108 namely:

GASEXP/4096 computes the percent used for the adjustment.

In step 110, if a COADJUST Factor exceeds 50, 50% degrading of sensitivity has occurred. In this event, then the CO trouble indicator is set.

In step 112, the sensitivity is adjusted.

If desired, temperature compensation can be incorporated into the method 100. In this regard in step 116, temperature is sensed. If less than a predetermined threshold indicated by numeral 20, then in step 118, the CO value can be compensated by the temperature value if it is less than 20° C. Positive sensitivity changes above 20° C. can be tolerated without compensation.

Those of skill in the art will understand that variations in the above processing can be made without departing from the spirit and scope of the invention. For example, it may be determined that the degrading rate, instead of merely representing a 5% value, is related to the degree of exposure. In such an event, a non-linear equation may represent a more accurate determination of the GASEXP factor. It may also be determined that the ambient temperature at the time of the gas exposures affects the degrading. Hence, it can be included as one of the variables in the determination for example, GASEXP=f(CO, TEMP).

The generation of alarm and trouble separately enables the system to which the detector, such as detector 10, is coupled to exhibit a proper response to the detector's condition. The output indications can be transmitted in communication messages, different wireless patterns, or different audio patterns which are emitted from the detector 10.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A sensor comprising:
   a gas sensing element which ages at two different rates, one rate occurs during a non gas exposure condition, the second rate occurs during a gas exposure condition; and
   circuitry coupled to the element, responsive to the two aging rates, where the circuitry includes executable instructions to assess the two aging rates and to process them to form at least one age compensating indicium.

2. A sensor as in claim 1 where the sensing element comprises an electro-chemical sensing element.

3. A sensor as in claim 1 where the instructions process the aging rates by carrying out a summing function.

4. A sensor comprising:
a gas sensing element which ages at two different rates, one rate occurs during a non gas exposure condition, the second rate occurs during a gas exposure condition;
circuitry coupled to the element, responsive to the two aging rates, for compensating therefor;
which includes software to evaluate an adjustment factor where the software compares the adjustment factor to a predetermined threshold; and
where the adjustment factor incorporates a predetermined aging parameter.

5. A sensor as in claim 4 where the aging parameter is one of a constant or a variable function of time.

6. A sensor as in claim 4 where the software responds to ambient temperature.

7. An apparatus comprising:
an electro-chemical sensor having an output signal;
circuitry coupled to the output signal and responsive to stochastic noise therein to adjust a signal processing parameter associated with that signal;
software for adjusting sensitivity in response to both gas and non-gas exposure; and
where the circuitry includes a gain adjusting circuit responsive to the stochastic noise.

8. An apparatus as in claim 7 where the gain adjusting circuit comprises at least one of an adjustable amplifier, or, a programmable processor.

9. An apparatus as in claim 8 which includes circuitry to compare a current stochastic noise parameter to a pre-stored parameter with the gain adjusting circuit responsive thereto.

10. An apparatus as in claim 8 which includes temperature compensation of the noise.

11. An apparatus as in claim 8 where the gain adjusting circuit alters a gain parameter inversely with respect to variations in the stochastic noise.

12. An apparatus comprising:

an electro-chemical sensor having an output signal;

circuitry coupled to the output signal and responsive to stochastic noise therein to adjust a signal processing parameter associated with that signal;

software for adjusting sensitivity in response to both gas and non-gas exposure; and where the software carries out a sensor adjustment, at least in part based on a predetermined aging function.

13. An apparatus comprising:

an electro-chemical sensor having an output signal;

circuitry coupled to the output signal and responsive to stochastic noise therein to adjust a signal processing parameter associated with that signal;

software for adjusting sensitivity in response to both gas and non-gas exposure; and which includes executable instructions to accumulate gas and non-gas exposure over time.

* * * * *